(12) United States Patent
Greenberg et al.

(10) Patent No.: US 9,656,059 B2
(45) Date of Patent: *May 23, 2017

(54) COCHLEAR STIMULATION DEVICE

(71) Applicant: Second Sight Medical Products, Inc., San Fernando, CA (US)

(72) Inventors: Robert J Greenberg, Los Angeles, CA (US); David D Zhou, Saugus, CA (US); Jordan Matthew Neysmith, Pasadena, CA (US); Kelly H McClure, Simi Valley, CA (US); Jianing Wei, Valencia, CA (US); Neil H Talbot, La Crecenta, CA (US); James S Little, Newhall, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 99 days.

This patent is subject to a terminal disclaimer.

(21) Appl. No.: 14/517,638

(22) Filed: Oct. 17, 2014

(65) Prior Publication Data

US 2015/0051684 A1    Feb. 19, 2015

Related U.S. Application Data

(62) Division of application No. 12/267,489, filed on Nov. 7, 2008, now Pat. No. 8,874,239.

(60) Provisional application No. 60/986,549, filed on Nov. 8, 2007.

(51) Int. Cl.
*A61N 1/05*    (2006.01)
*A61N 1/04*    (2006.01)

(52) U.S. Cl.
CPC .......... *A61N 1/0541* (2013.01); *A61N 1/0472* (2013.01)

(58) Field of Classification Search
CPC ...... A61N 1/04; A61N 1/0472; A61N 1/0476; A61N 1/0484; A61N 1/05; A61N 1/0541
See application file for complete search history.

(56) References Cited

U.S. PATENT DOCUMENTS

| 5,109,844 A | 5/1992 | de Juan, Jr. et al. |
| 5,935,155 A | 8/1999 | Humayun et al. |
| 6,400,989 B1 | 6/2002 | Eckmiller |

(Continued)

FOREIGN PATENT DOCUMENTS

WO    WO 2008/103195 A2    8/2008

*Primary Examiner* — Eric D. Bertram
*Assistant Examiner* — Elizabeth K So
(74) *Attorney, Agent, or Firm* — Scott Dunbar

(57) ABSTRACT

A cochlear stimulation device comprising an electrode array designed to provide enhanced charge injection capacity necessary for neural stimulation. The electrode array comprises electrodes with high surface area or a fractal geometry and correspondingly high electrode capacitance and low electrical impedance. The resultant electrodes have a robust surface and sufficient mechanical strength to withstand physical stress vital for long term stability. The device further comprises wire traces having a multilayer structure which provides a reduced width for the conducting part of the electrode array. The cochlear prosthesis is attached by a grommet to the cochleostomy that is made from a single piece of biocompatible polymer. The device, designed to achieve optimum neural stimulation by appropriate electrode design, is a significant improvement over commercially available hand-built devices.

10 Claims, 10 Drawing Sheets

(56) References Cited

U.S. PATENT DOCUMENTS

| | | |
|---|---|---|
| 6,458,157 B1 | 10/2002 | Suaning |
| 7,684,868 B2 * | 3/2010 | Tai .......................... H01F 7/06 607/54 |
| 2003/0097165 A1 | 5/2003 | Krulevitch et al. |
| 2004/0030376 A1 * | 2/2004 | Gibson ................ A61N 1/0541 607/137 |
| 2006/0003090 A1 | 1/2006 | Damien et al. |
| 2006/0247754 A1 | 11/2006 | Greenberg et al. |
| 2007/0106360 A1 * | 5/2007 | Gibson ................ A61N 1/0541 607/137 |
| 2007/0293749 A1 | 12/2007 | Zhou et al. |

* cited by examiner

COCHLEAR STIMULATION DEVICE

CROSS-REFERENCE TO RELATED APPLICATIONS

This application is a divisional application of U.S. patent application Ser. No. 12/267,489, now U.S. Pat. No. 8,874, 239 filed Nov. 7, 2008, for Cochlear Stimulation Device, which claims the benefit of U.S. Provisional Application No. 60/986,549 "Cochlear Stimulation Device", filed Nov. 8, 2007, the disclosure of which is incorporated herein by reference. This application is related to and incorporates by reference the following commonly assigned patent applications: 2004/0220652, filed Nov. 4, 2004 for Adherent Metal Oxide Coating Forming a High Surface Area Electrode; 2006/0247754, filed Nov. 2, 2006 for Flexible Circuit Electrode Array; 2007/0092750, filed Apr. 26, 2007 for Electrode Surface Coating and Method for Manufacturing the Same; and 2008/0221653, filed Sep. 11, 2008, for Flexible Circuit Electrode Array.

GOVERNMENT RIGHTS NOTICE

This invention was made with government support under grant No. R24EY12893-01, awarded by the National Institutes of Health. The government has certain rights in the invention.

FIELD OF THE INVENTION

The present invention relates to cochlear stimulation device, that improves a cochlear electrode array of the implanted portion of the system.

BACKGROUND OF THE INVENTION

Human deafness results from numerous factors including trauma, ear infections, congenital factors, toxic effects of some antibiotics, and from diseases such as meningitis. Sensorineural damage (damage to the hair cells in the cochlea) is the largest single form of hearing loss. In a healthy ear these hair cells convert acoustic signals in the inner ear to electrical signals that can be interpreted by the brain as sound. It is estimated that over 7% of the U.S. population is affected by sensorineural deafness, and one in a thousand infants is born totally deaf. Extrapolating these percentage figures, it is estimated that there are 30 million people in the world who are profoundly deaf.

Considerable research over the past several decades has been directed towards developing a means to bypass the non-functioning hair cells in the inner ear (or cochlea) by using electrodes to directly stimulate auditory afferent neurons within the cochlea. This so called cochlear implant technology has progressed from early methods of attaching one or more single wire electrodes onto the promontory or the bony shell of the cochlea, to drilling directly into the cochlea, and inserting electrodes into the scalae therein. Electrodes used in modern cochlear prostheses generally use a longitudinal monopolar (or bipolar) electrode configuration where small platinum/iridium plates or circular platinum rings connected internally by thin wires, with the electrodes and wires held together in a smooth elongated silicone carrier, are surgically implanted into the scala tympani (one of the canals within the cochlea), via a hole made in the mastoid bone behind the ear. Entry into the scala tympani is generally via the round window membrane. The electrodes are electrically connected to an electronics package anchored in a cavity made in the mastoid bone. Information is sent to this internal electronics package transcutaneously, via RF transmission across the skin barrier, from an external body-worn (generally behind the ear) electronics package that houses the speech processor, control electronics and power supply.

Current cochlear implant systems include an implant portion and an external portion. The implant portion typically includes: (1) an electrode array, (2) an implanted coil and (3) a hermetically-sealed housing to which the electrode array and implanted coil are attached and in which electronic circuitry, e.g., data processing circuitry and pulse generator circuitry are housed. The external portion typically includes: (1) a microphone, (2) a battery-powered sound processor for processing the signals sensed by the microphone and for generating control and other signals that are transmitted to the implant portion and (3) a headpiece, connected to the sound processor by way of a cable or wire(s), in which an external coil is housed. In operation, the headpiece coil (external coil) is inductively coupled with the implanted coil so that power and data can be transferred to the implant portion from the external portion.

U.S. Pat. No. 5,123,422 teaches the use of internal hinges or slits, where such hinges or slits are oriented to give flexibility in only one plane, and can be inserted in the scala tympani without curling, thus orienting the electrode sites "to obtain good stimulation of the nerve cells". U.S. Pat. No. 4,261,372 uses "V" shaped notches along one side of the array to permit the array to assume the required curved shape within the scala, and to obtain greater insertion depth of the electrodes by first inserting one part of the electrode into the first turn of the scala tympani and then inserting the other part into the second turn of the scala tympani. U.S. Pat. No. 4,832,051 describes an electrode device where "the elements are resiliently attached together so that the stack of elements is stiff in compression along the common axis and is flexible in tension." Cochlear stimulation devises have been further described in U.S. Pat. Nos. 7,194,314, 7,085,605, 6,906,262, 6,782,619, 6,678,564, or 6,374,143.

The electrode is an important part of cochlear implant system because it affects the current spread and the response of the auditory nerves. Modern technology uses multichannel (electrode) implants as opposed to single electrode implants, as the former provides electrical stimulation at multiple sites in the cochlea using an array of electrodes. An electrode array is used so that different auditory nerve fibers can be stimulated at different places in the cochlea, thereby exploiting the place mechanism for coding frequencies. Different electrodes are stimulated depending on the frequency of the signal. Electrodes near the base of the cochlea are stimulated with high frequency signals, while electrodes near the apex are stimulated with low frequency signals. The design of the electrode array are important with regard to the electrode placement, number of electrodes and spacing between electrodes, orientation of electrodes with respect to the excitable tissue and electrode configuration. The electrodes are commonly placed in the scala tympani because it brings the electrodes in close proximity with auditory neurons which lie along the length of the cochlea and thereby preserves the place mechanism for coding frequencies. The larger the number of electrodes, the finer the place resolution for coding frequencies. However, using a large number of electrodes will not necessarily result in better performance, because frequency coding is constrained by the number of surviving auditory neurons that can be stimulated. Studies have shown that for adequate speech perception, at least 8 electrodes are required.

Commercially available cochlear implant devices comprise simple tapered longitudinal bipolar and monopolar electrode arrays using small platinum/iridium balls or circular rings. However these devices were developed taking into consideration the ease of fabrication as well as surgical insertibility rather than the critical design parameters necessary to achieve optimum neural stimulation. They continue to be hand built under a microscope and are made using wire based technologies. There is, therefore, still a need in the art to improve the currently available cochlear stimulation devices by appropriate electrode design consideration.

The present invention is an improvement over the known commercial devices. The device comprises an electrode array designed to increase the current transfer capability of the electrodes by using high surface area electrodes without increasing the geometrical surface area. Since an implantable stimulation or sensing electrode is intended for long term use in a neural stimulator with a low power consumption and limited compliance voltages, it requires high electrode capacitance and correspondingly low electrical impedance. Without sufficiently low impedance, a large voltage may cause polarization of both the electrode and the tissue to which the electrode is attached forming possible harmful byproducts, degrading the electrode and damaging the tissue.

BRIEF SUMMARY OF THE INVENTION

The present invention is directed to a cochlear stimulation device in various embodiments. The device comprises an electrode array suitable for attaching to the cochlea, wire traces and a polymer body.

A layer of polymer is laid down, commonly by some form of chemical vapor deposition, spinning, meniscus coating or casting. A layer of metal, preferably platinum, and more preferably platinum grey, which has a fractal geometry, is applied to the polymer and patterned to create electrodes and leads for those electrodes. The electrodes can contain Pt, Ir, Au, Ru, Rh, Pd, C, conducting polymers or alloys or oxides thereof. In an alternative embodiment, the platinum grey fractal surface is coated with either a gradient or discrete coating of an inert material, such as iridium oxide. The electrodes have a rough surface and hence a very large surface area when compared to an electrode with a smooth metal surface having the same geometric shape. Because of the rough surface area, the electrodes have sufficient physical and mechanical strength to withstand physical stress. Additionally, the iridium oxide layer provides very high charge storage capacity for pulse stimulation. The method of making a high surface area coating is described in US Patent Application 2004/0220652 and 2007/0092750 both of which are assigned to the same assignee as is the present application, and which are incorporated herein by reference.

The novel feature of the invention is a cochlear stimulation device comprising an electrode array with a high surface area electrodes and metal leads which have a multilayer structure, preferably two or three layers. This variation allows a reduced width of the conducting cable of the electrode array. The advantage is that the electrode density is increased without increasing the array cable width or even with reduced cable width. The conducting part can be made narrower by slight increase of the thickness.

The method of making an flexible electrode array as applied to retinal stimulation is described in US patent Application US 2006/0247754 which is assigned to the same assignee as is the present application, and which is incorporated herein by reference.

OBJECTS OF THE INVENTION

It is an object of the invention to provide a cochlear stimulation device comprising an electrode array wherein the surface area of the individual electrodes in the array is high for a given geometrical electrode size thereby enhancing the charge transfer capability of the electrodes.

It is also an object of the present invention to use a series of new electrode geometries that control charge transfer characteristics by the strategic use of edges and corners to concentrate current delivery.

It is also an object of the present invention to use a multilayer structure for the metal traces. The traces require this way a smaller width than traces without multi leads. In one embodiment, the two leads or traces on the right and left side of the electrode array lead to electrodes preferably on different levels of the array. In another embodiment, the upper half and the lower half are cut vertically and are in two different layers. In yet another embodiment, the two halves are placed next to each other. The advantage of the present multilayer is that the conductivity stays stable because even if the electrode starts to dissolve at the edge to the insulating material the conductivity stays stable until the electrode dissolves completely towards the center. Vias can be used to connect traces on different metal layers or to connect an electrode to a metal a trace.

Other objects, advantages and novel features of the present invention will become apparent from the following description of the invention when considered in conjunction with the accompanying drawing.

BRIEF DESCRIPTION OF THE SEVERAL VIEWS OF THE DRAWINGS

The preferred and alternative embodiments of the invention will be described by references to the accompanying drawings, in which.

DETAILED DESCRIPTION OF THE INVENTION AND BEST MODE OF PRACTISING THE INVENTION

Polymer materials are useful as electrode array bodies for neural stimulation. They are particularly useful for retinal stimulation to create artificial vision, cochlear stimulation to create artificial hearing, or cortical stimulation for many purposes. Regardless of which polymer is used, the basic construction method is the same. A layer of polymer is laid down, commonly by some form of chemical vapor deposition, spinning, meniscus coating or casting. A layer of metal, preferably platinum, is applied to the polymer and patterned to create electrodes and leads for those electrodes. Patterning is commonly done by photolithographic methods. A second layer of polymer is applied over the metal layer and patterned to leave openings for the electrodes, or openings are created later by means such as laser ablation. Hence the array and its supply cable are formed of a single body. Alternatively, multiple alternating layers of metal and polymer may be applied to obtain more metal traces within a given width.

To achieve the accurate place coding of frequency through multiple-electrode stimulation, the electrodes have to be placed below the sense organ for hearing (scala tympani) and close to the ganglion cells at the center of the inner ear. But placement of the electrodes in the inner ear could possibly damage the very nerves that were intended to stimulate. In order to minimize the risk of surgical trauma to the nerves, the electrodes should have the right mechanical properties. They need to be smooth, tapered and flexible at the tip and stiffer towards the proximal end. The edges of a flexible circuit polymer array may be quite sharp and cut the delicate neural tissue. Common flexible circuit fabrication techniques such as photolithography, generally require that a flexible circuit electrode array be made flat. With most polymers, it is possible to curve them when heated in a mold. By applying the right amount of heat to a completed array, a helical shape can be induced to approximate the shape of the cochlea. With a thermoplastic polymer such as liquid crystal polymer, it may be further advantageous to repeatedly heat the flexible circuit in multiple molds, each with a decreasing radius. Further, it is advantageous to add material along the edges of a flexible circuit array. Particularly, it is advantageous to add material that is more compliant than the polymer used for the flexible circuit array.

Figure 1:
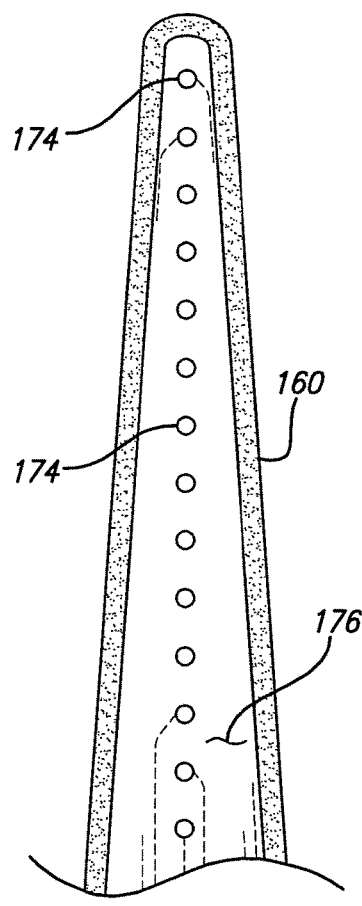
FIG. 1 shows a top view of a cochlear electrode array with circular shaped electrodes according to the present invention.
Figure 1A:
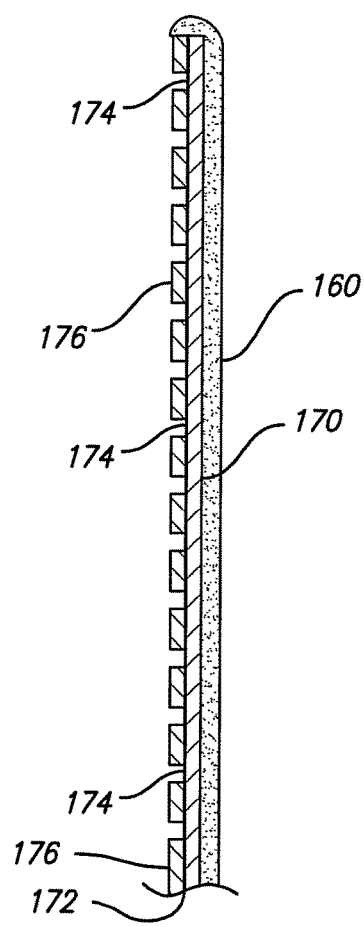
FIG. 1A shows a cross sectional view of a cochlear electrode array according to the present invention.

FIGS. 1, 1A, 2, 6 and 7 show application of the present invention to a cochlear prosthesis. FIG. 1 shows of top view of cochlear electrode array 110. The cochlear electrode array 110 tapers toward the top to fit in an ever smaller cochlea and because less width is required toward the top for metal traces. The electrodes 174 are arranged linearly along the length of the array 110. Further a skirt 160 of more compliant polymer, such as silicone surrounds the array 110. FIG. 1A is a cross sectional view of the cochlear electrode array 110. The cochlear electrode array 110 includes a bottom polymer layer 170, metal traces 172 and a top polymer layer 176. Openings in the top polymer layer 176 define electrodes 174.

Figure 5:
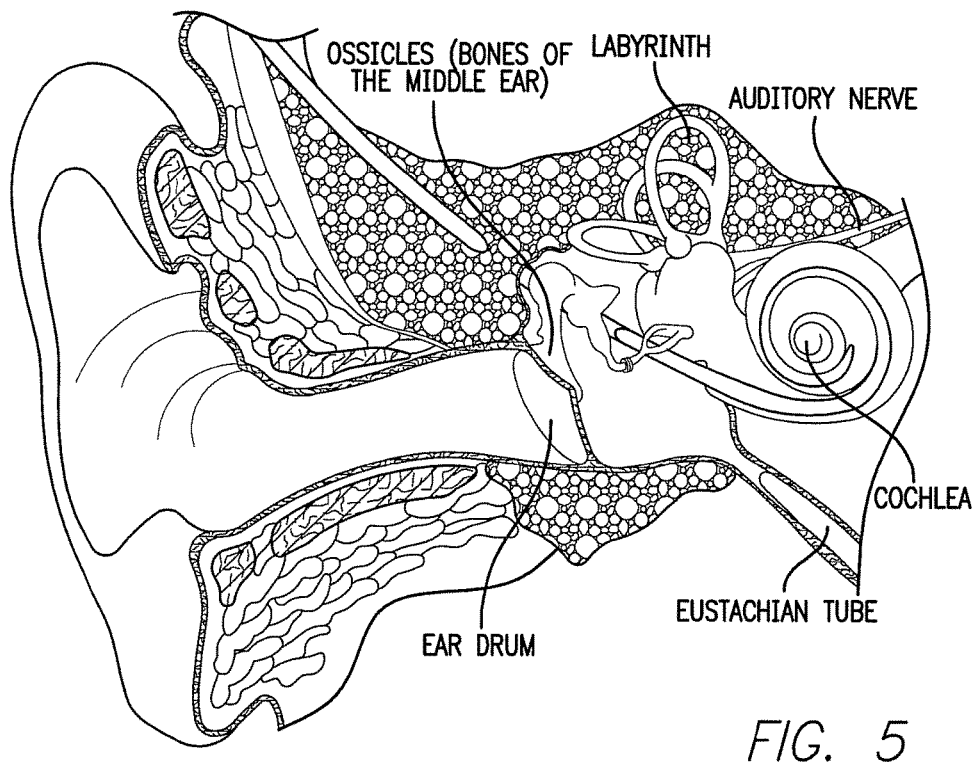
FIG. 5 shows a cross sectional view of a human ear.
Figure 6:
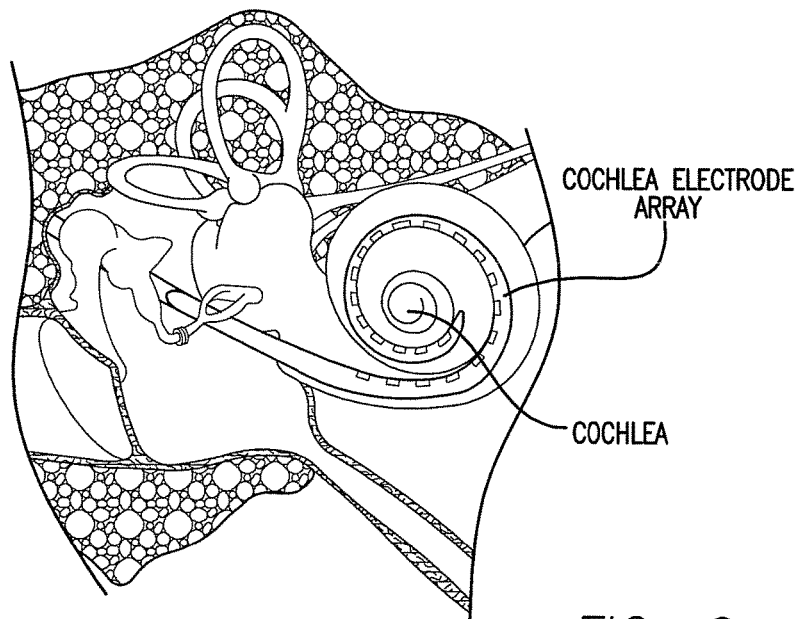
FIG. 6 shows a cross sectional view of a cochlear electrode array according to the present invention as implanted in the cochlea.
Figure 7:
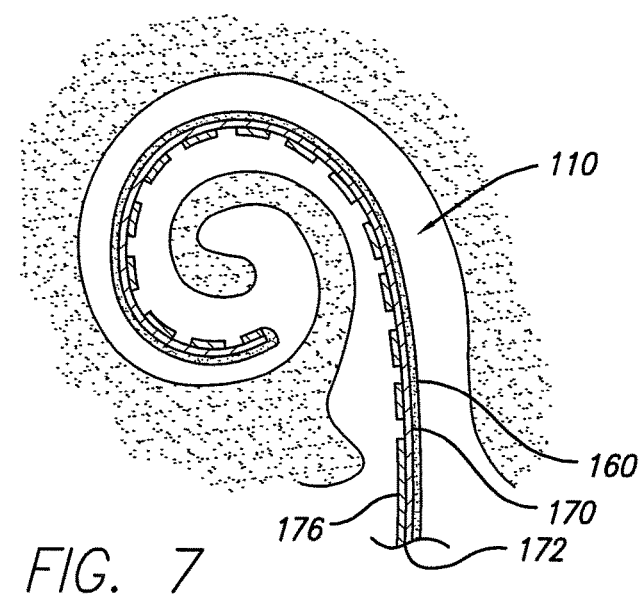
FIG. 7 shows a cross sectional view of a cochlear electrode array according to the present invention as implanted in the cochlea.
Figure 18:
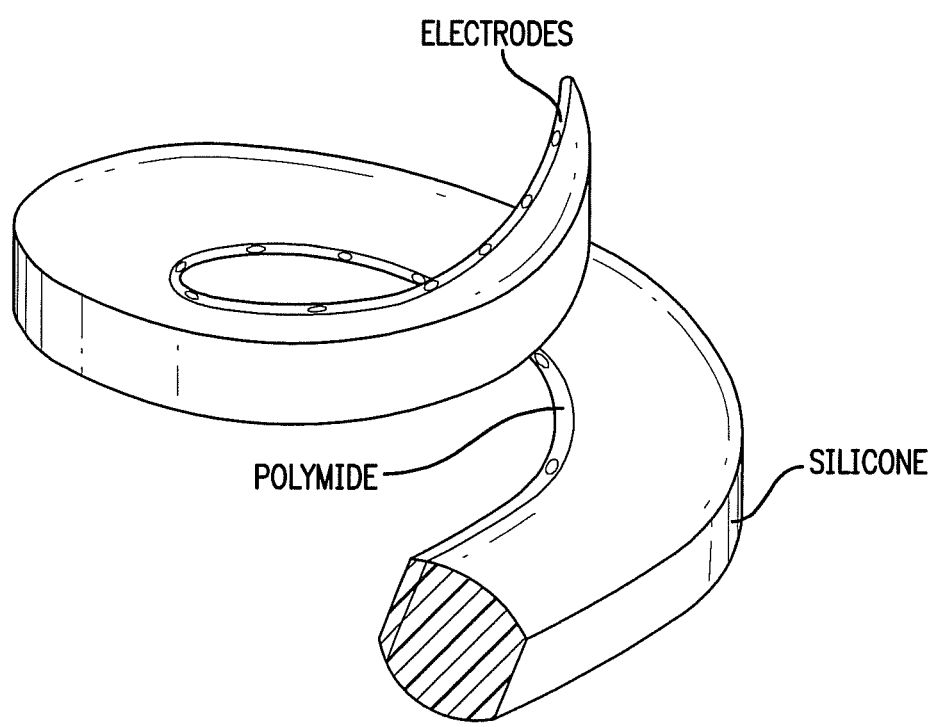
FIG. 18 shows top view of a cochlear prosthesis silicone molded into a helical shape.

The cochlear electrode array 110 is made flat as shown in FIGS. 1A, 6 and 7. It is then thermoformed, as described above, into a spiral shape to approximate the shape of the cochlea, as shown in FIGS. 5, 6 and 18. FIG. 18 shows how cochlear prosthesis can be molded in a silicone mold to maintain a helix structure. The cochlear electrode array 110 is implanted with the bottom layer 170 formed towards the outside of the curvature, and the top polymer layer 176 toward the inside of the curvature. This is opposite of the thermoforming process used for a retinal array. A cortical array would be thermoformed to curve inward like a cochlear array.

Figure 2:
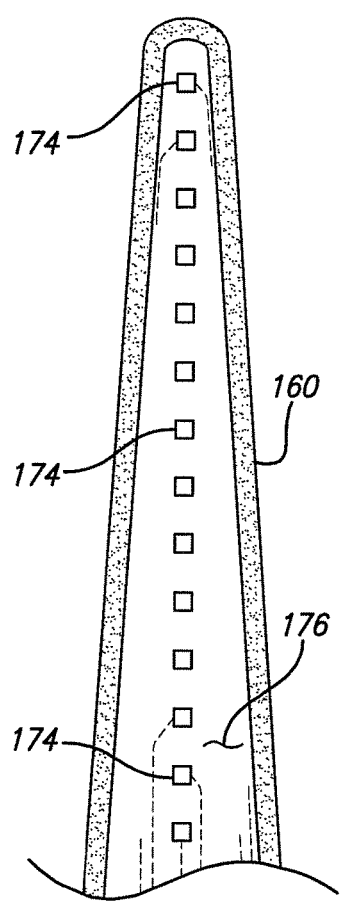
FIG. 2 shows a top view of a cochlear electrode array with square shaped electrodes according to the present invention.

FIG. 1 shows circular shaped electrodes as a preferable embodiment. FIG. 2 shows square shaped electrodes as preferred embodiment. Circle shapes, star shapes, square shapes and rings can be used in the electrode array. Each of the shapes can contain overlapping edges and mesh grids. This presents a series of new electrode geometries that control charge transfer characteristics by the strategic use of edges and corners to concentrate current delivery. These designs are an improvement on conventional surface electrode designs which are typically circles. The electrodes can contain Pt, Ir, Au, Ru, Rh, Pd, C, conducting polymers or alloys or oxides thereof. The electrodes contain preferably platinum and more preferably platinum gray.

Platinum gray's color density values range from 0.4 D to 1.3 D, while platinum black and shiny platinum both have color density values greater than 1.3 D.

Platinum gray can be distinguished from platinum black based on the adhesive and strength properties of the thin film coating of the materials. Adhesion properties of thin film coatings of platinum gray and platinum black on 500 microns in diameter electrodes have been measured on a Micro-Scratch Tester (CSEM Instruments, Switzerland). A controlled micro-scratch is generated by drawing a spherical diamond tip of radius 10 microns across the coating surface under a progressive load from 1 millinewton to 100 millinewtons with a 400 micron scratch length. At a critical load the coating will start to fail. Using this test it is found that platinum gray can have a critical load of over 60 millinewtons while platinum black has a critical load of less than 35 millinewtons.

Electrodes with a surface layer of platinum gray are prepared using constant voltage plating. The most preferable voltage range to produce platinum gray has been found to be −0.45 Volts to −0.85 Volts. Applying voltage in this range to the plating solution (preferably 3 to 30 mM ammonium hexachloroplatinate in disodium hydrogen phosphate) yields a plating rate in the range of about 1 micron per minute to 0.05 microns per minute, the preferred range for the plating rate of platinum gray. Constant voltage control also allows an array of electrodes in parallel to be plated simultaneously achieving a fairly uniform surface layer thickness for each electrode. Surface area increase of platinum grey calculated from the electrode capacitance is about 50 to 500 times the surface area resulting from the basic geometrical. This increased electrode surface area of platinum grey in the electrode array of the cochlear implant device significantly enhances charge injection capacity necessary for stimulation. Further the robust surface of the resultant electrode brought about by electroplating of platinum gray imparts the mechanical strength that is vital for long term use of the cochlear device.

Furthermore, it has been found that because of the physical strength and low stress of platinum gray, it is possible to plate surface layers of thickness greater than 30 microns. It is very difficult to plate shiny platinum in layers greater than approximately several microns because the internal stress of the dense platinum layer which will cause the plated layer to peel off and the underlying layers cannot support the above material. The additional thickness of the plate's surface layer allows the electrode to have a much longer usable life.

In an alternative embodiment, the platinum grey fractal surface is coated with either a gradient or discrete coating of an inert material, such as iridium oxide. Iridium oxide coats the fractal surface of the platinum gray with a cauliflower-like morphology with feature sizes ranging from 0.5 to 15 microns. Each branch of such structure is further covered by smaller and smaller features of similar shape. The features particles on the surface layer may be in the nanometer range. This rough and porous fractal structure increases the electrochemically active surface area of the platinum surface when compared to an electrode with a smooth platinum surface having the same geometric shape. This iridium oxide layer provides very high charge storage capacity for pulse stimulation. The most preferable voltage range to produce adherent iridium oxide has been found to be +0.45V to +0.65V. Applying voltage in this range with the above solution 13 yields a plating rate of about 2 to 4 mC/cm.sup.2/min, which is the preferred range for the plating rate of iridium oxide.

A comparison of the impedance spectra for different surfaces indicates that the electrode impedance decreased after rough platinum plating and was further reduced after iridium oxide plating on the rough platinum surface. The charge storage capacity measured in the electrode's capacitance, which is proportional to the electrode surface area, was determined to increase more than 200 times for the iridium oxide plated surface, as compared with unplated electrodes of the same diameter.

The traces contain preferably Pt as conductive layer. Adhesion layers containing preferably Ti can be applied on the top, the bottom or on both sides of the conductive layer. Such a sandwich layer containing Ti/Pt/Ti has a thickness of about 5000 Å. The polyimide separation layer has a thickness of about 5 µm.

Figure 3:
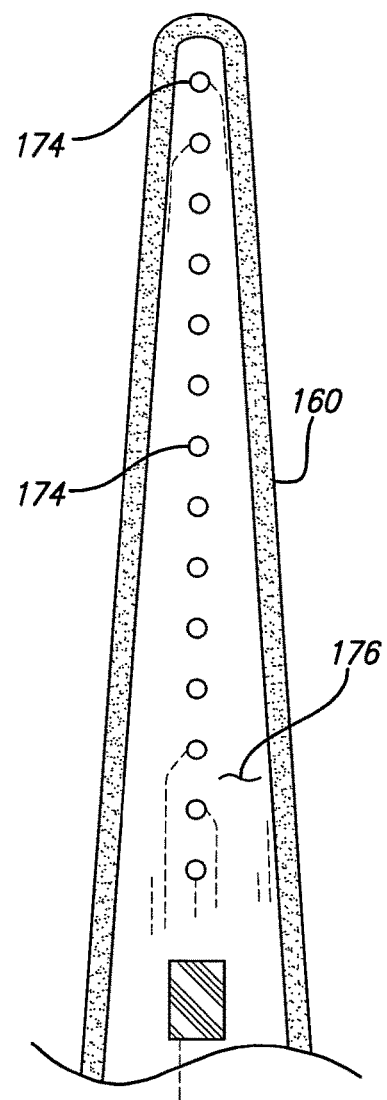
FIG. 3 shows a top view of a cochlear electrode array according to the present invention with a return/ground electrode on the entry level.
Figure 4:
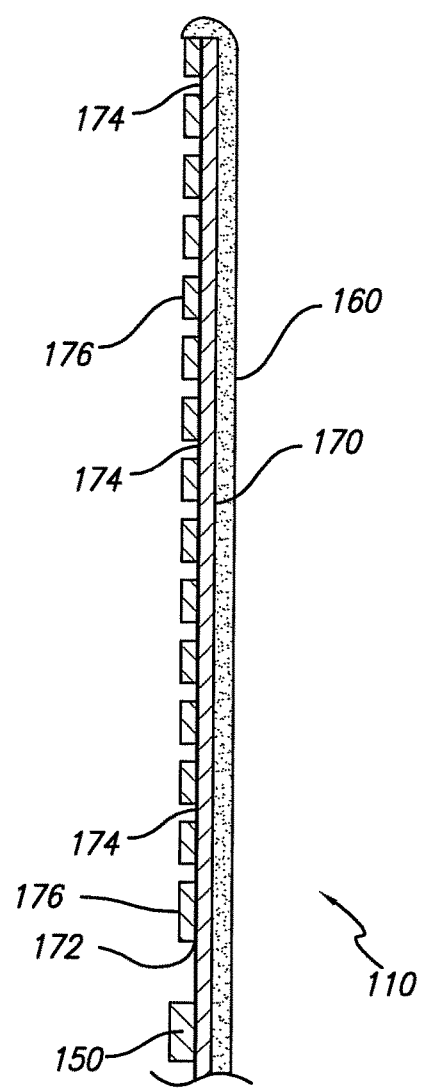
FIG. 4 shows a cross sectional view of a cochlear electrode array according to the present invention with a return/ground electrode on the entry level.

FIG. 3 shows a top view of a cochlear electrode array according to the present invention with a return/ground electrode 150 on the entry level. FIG. 4 shows a cross sectional view of a cochlear electrode array according to the present invention with a return/ground electrode on the entry level. An electrode array must have a return, or common, electrode to make a complete circuit with the neural tissue. It is advantageous that the return electrode is large and in tissue less sensitive to electrical stimulation to avoid stimulating tissue with the return electrode.

The return electrode is coupled by a cable to a contact pad for attaching the return electrode to the electronics package. FIG. 3 shows the preferred electrode array with the return electrode 150 on front of the cable inside the eye. FIG. 4 is the preferred electrode array with the return electrode 150 on the back of the cable outside the eye. The return electrode 150 should be provided in a mesh, star pattern or hash pattern to reduce the eddy current effect on the coil. It would also be advantageous to provide more than one of the return electrodes described herein and provide a switch mechanism to switch between or utilize more than one. This way a user could select the configuration that is most comfortable for them.

Figures 8, 8A:
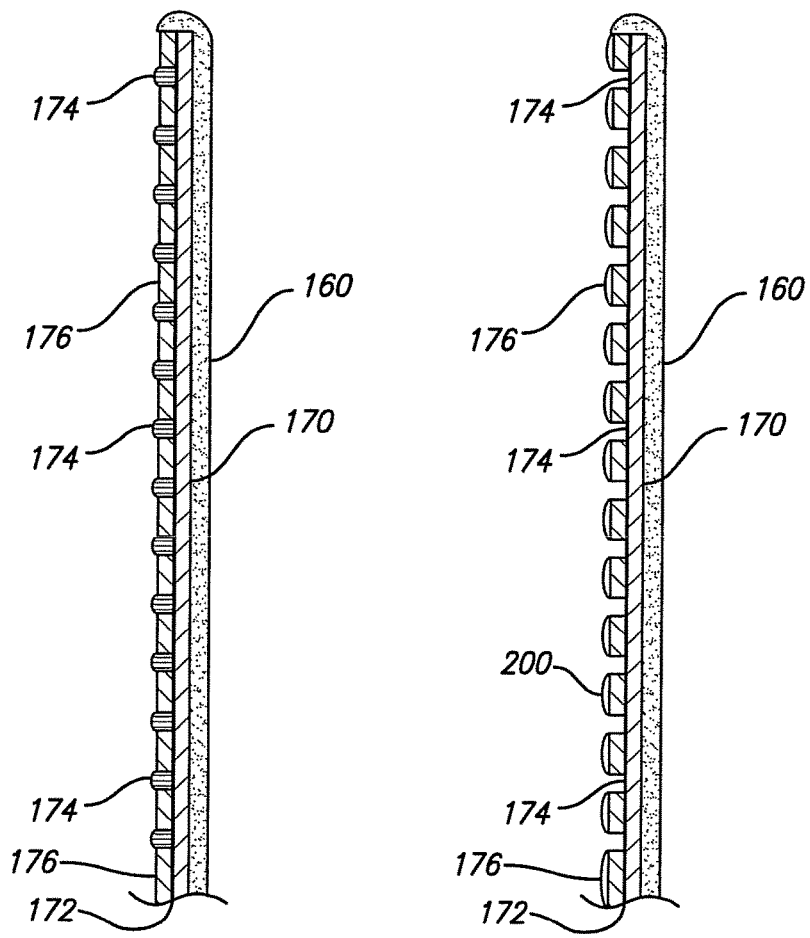
FIG. 8 shows a cross sectional view of a cochlear electrode array according to the present invention with elevated electrodes.
FIG. 8A shows a cross sectional view of a cochlear electrode array with recessed electrodes and silicone bumps between the electrodes according to the present invention with elevated electrodes.
Figures 8B, 8C, 8D:
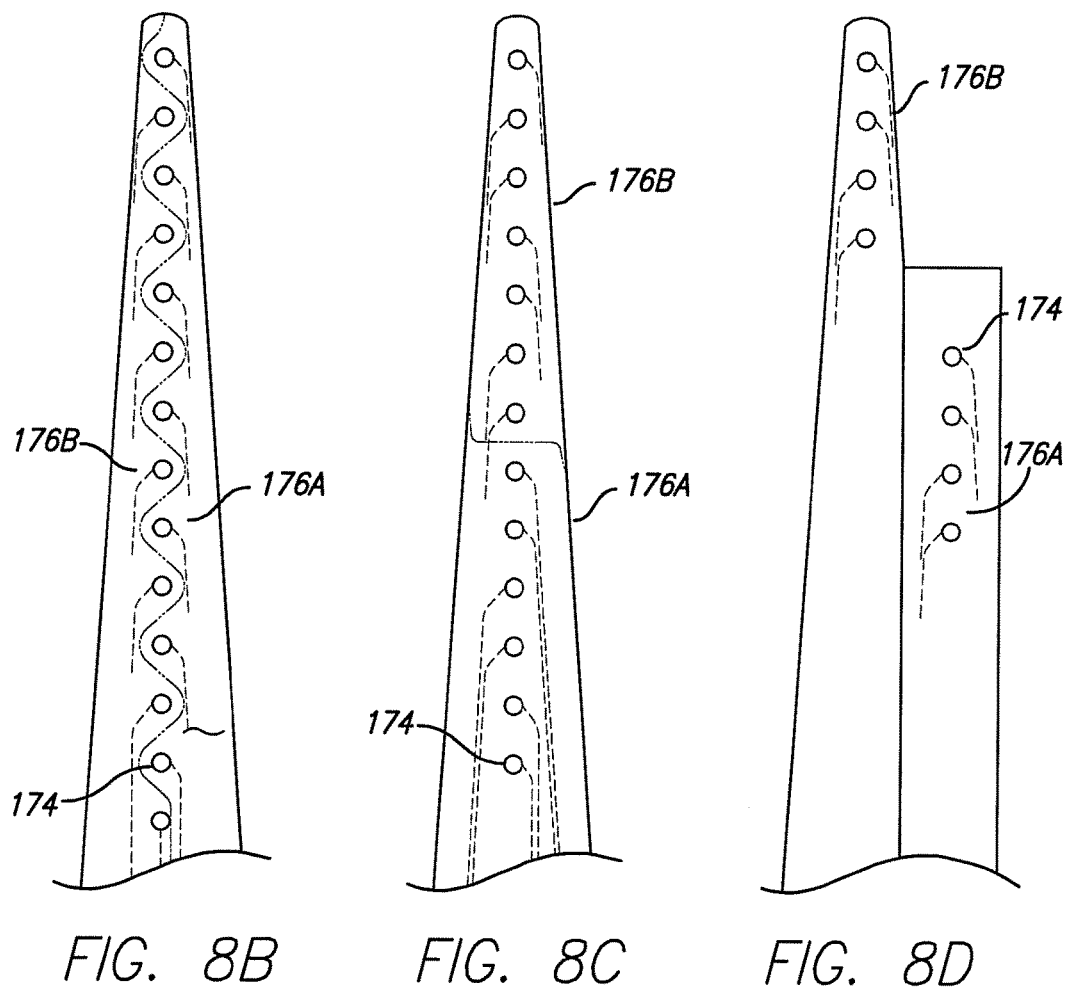
FIG. 8B shows a top view of a cochlear electrode with multiple leads according to the present invention with elevated electrodes.
FIG. 8C shows a top view of a cochlear electrode with another variation of the multi lead trace wires, wherein the upper half and lower half are cut vertically and are in different layers (176A layer 1 and 176 B layer 2).
FIG. 8D shows a top view of a cochlear electrode with another variation of the multi lead trace wires, wherein the two halves are placed next to each other (176A layer 1 and 176B layer 2).

FIG. 8 shows a cross sectional view of a cochlear electrode array according to the present invention wherein the electrodes 174 stick out of the polymer isolating layer. FIG. 8A shows a cross sectional view of a cochlear electrode array with recessed electrodes and silicone bumps between the electrodes according to the present invention with elevated electrodes. The obtained electrode array contains micro sticks or fillings of polymer, especially such containing silicone in the spaces between the electrodes. The edges of the electrodes can be covered by a grid or mesh of polymer to increase the adhesion and stability. Polymer can contain polyimide, silicone, peek or parylene, or mixtures thereof. Gaps can be filled in by polymer such as PDMS or epoxy wherein a plated soft low stress layer can be provided. It has been found that the silicone adhesion to the polyimide is better when small holes are applied to the polyimide surface prior to applying of silicone on that surface. FIG. 8B shows a top view of a cochlear electrode with multiple leads. The two leads or traces on the right end left side of the electrode array 176A and 176B lead to electrodes preferably on different levels of electrodes (176A layer 1 and 176B layer 2). FIG. 8C shows a different variation of the multi lead of the trace wires, wherein the upper half and lower half are cut vertically and are in different layers (176A layer 1 and 176B layer 2). FIG. 8D shows again a different variation wherein the two halves are placed next to each other (176A layer 1 and 176B layer 2). The traces require this way a smaller width than traces without multi leads.

Figure 11:
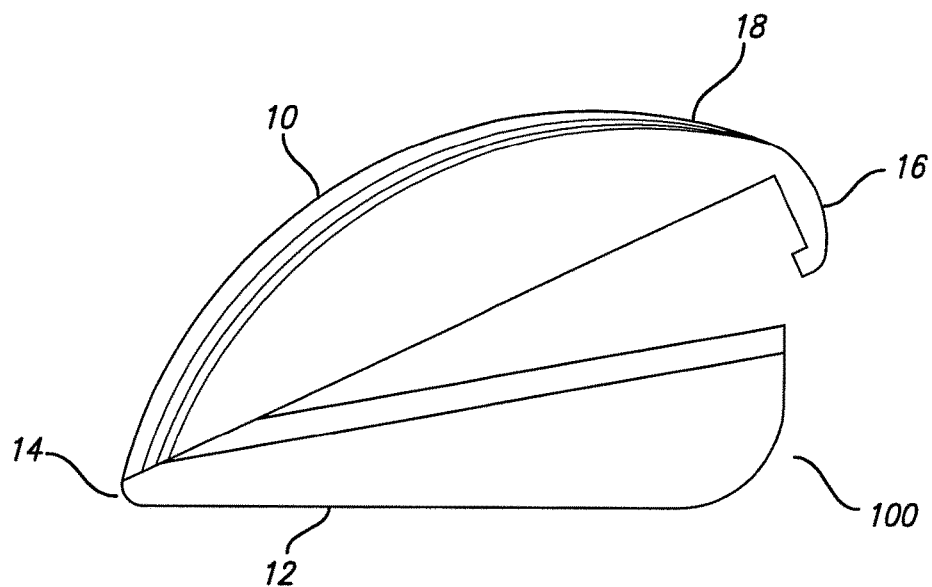
FIG. 11 shows a cross sectional view of a cochleostomy grommet according to the present invention.

FIG. 11 show the preferred cochleostomy grommet. The grommet includes an upper half 10 and a lower half 12, joined by a hinge 14. Preferably, the cochleostomy grommet is made from a single piece of biocompatible polymer such as polyimide and sufficiently narrowed at the hinge 14 to make it flexible. A snap type closure 16 is opposite the hinge. In addition, the grommet may include a grove 18, to facilitate tying a suture around the grommet.

Figure 9:
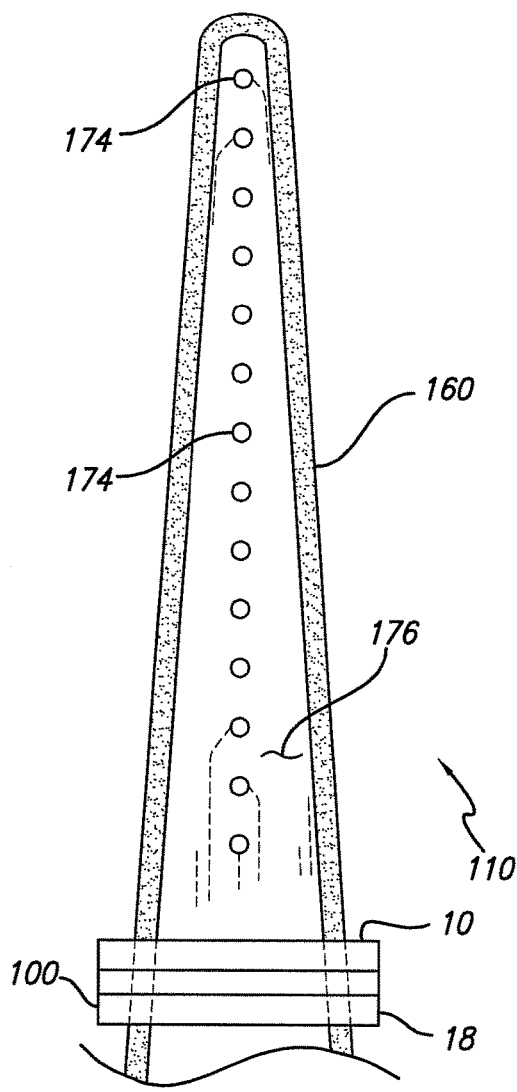
FIG. 9 shows of top view of a cochlear electrode array with a cochleostomy grommet according to the present invention.
Figure 10:
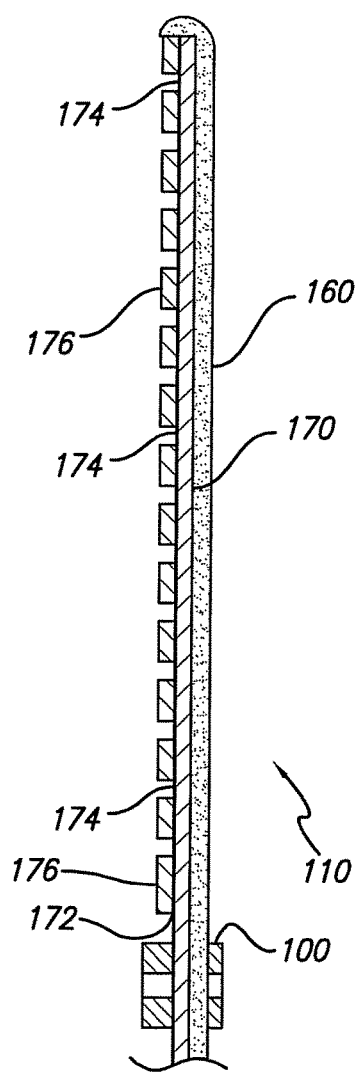
FIG. 10 shows a cross sectional view of a cochlear electrode array with a cochleostomy grommet according to the present invention.
Figure 12:
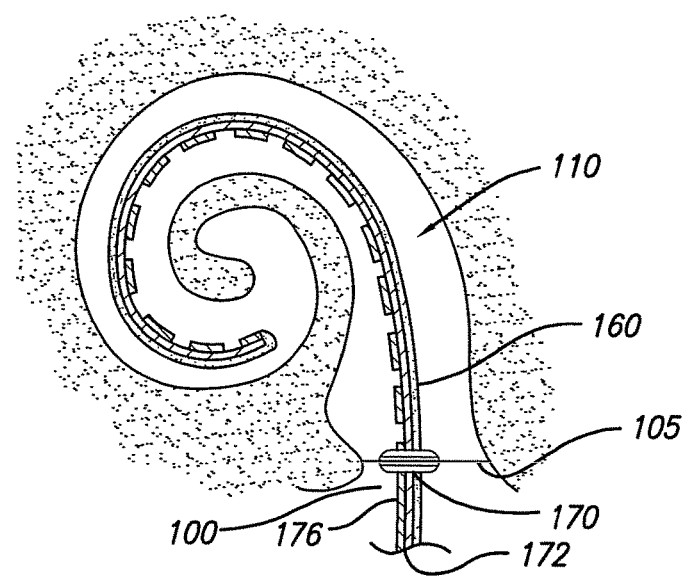
FIG. 12 shows of top view of a cochlear electrode array with a cochleostomy grommet in place according to the present invention.

FIGS. 9 and 10 show perspective views of the implanted portion of the preferred cochlear prosthesis with a grommet, 100 which is in place. FIG. 12 shows the cochlear prosthesis attached by the grommet to the cochleostomy.

Figure 13:
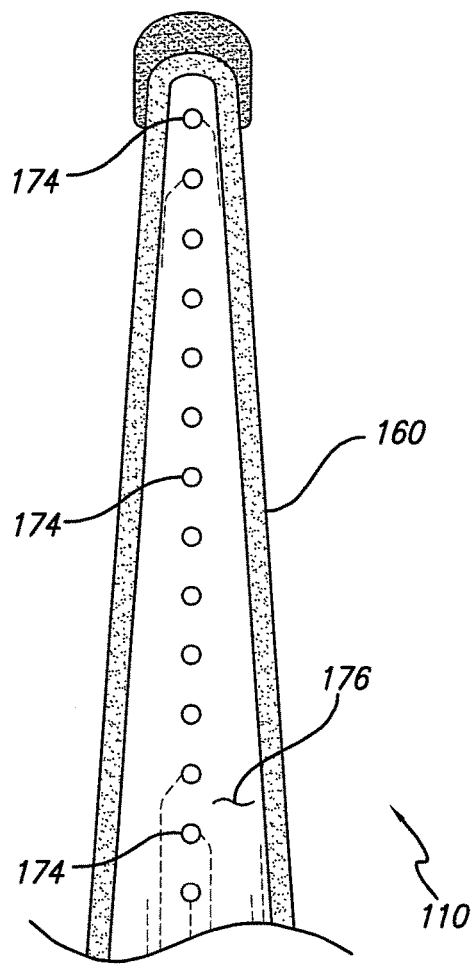
FIG. 13 shows a top view of a cochlear electrode array with a soft silicone tip according to the present invention.
Figure 14:
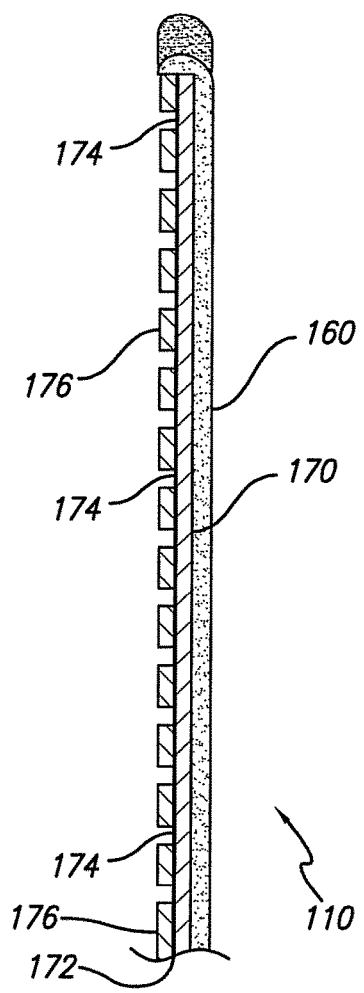
FIG. 14 shows a cross sectional view of a cochlear electrode array with a soft silicone tip according to the present invention.

FIGS. 13 and 14 show the implanted electrode array with a soft tip which preferably contains silicone. During insertion of the array into the cochlea, it is easy to cause surgical trauma. Silicone skirt 160 can be extended at the tip of the array to provide extra protection.

Figure 15:
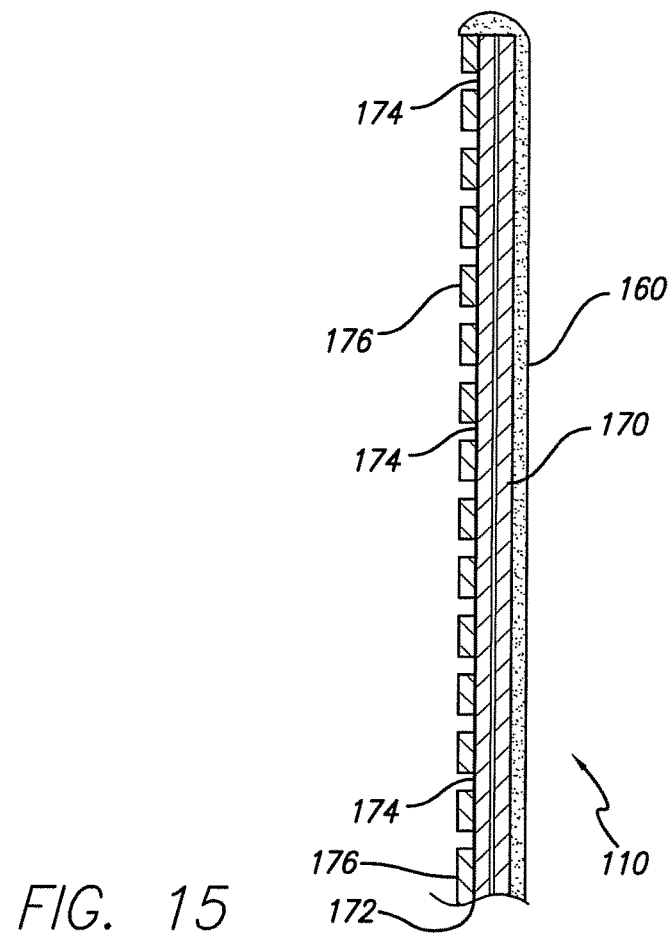
FIG. 15 shows a cross sectional view of a multilayer cochlear electrode array according to the present invention.
Figure 16:
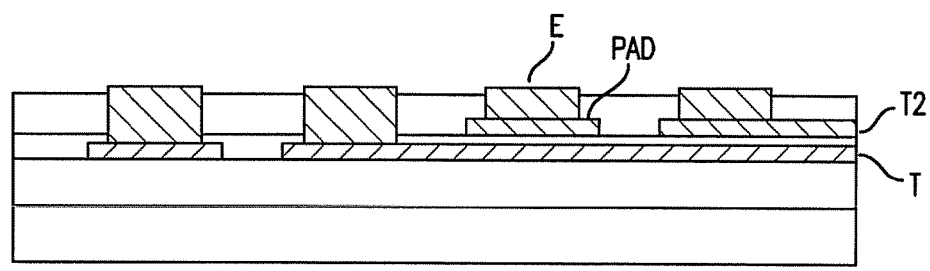
FIG. 16 shows a cross sectional view of a multilayer cochlear electrode array according to the present invention.
Figure 17:
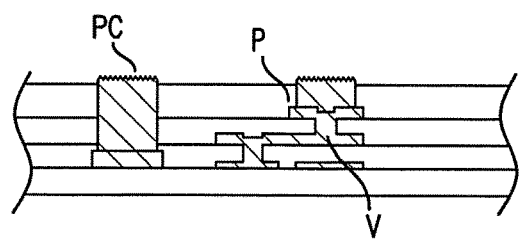
FIG. 17 shows a cross sectional view of a multilayer cochlear electrode array with interlayer vias to allow connections between the metal traces according to the present invention.

FIGS. 15-17 show a cross-section of multilayer structure. The traces (metal) are in more than one layer, preferably two or three layers. This variation allows a reduced width of the conducting part of the electrode array. The advantage is that the conducting density is increased. The conducting part can be made thinner by slight increase of the depth. The increase of the depth has only minor influence on the flexibility of the conducting part. FIG. 15 shows that the wire traces are separated by insulating polymer containing polyimide. FIG. 17 shows filled via leading into a conducting pad. The current enters the electrode through via in the center and not at the edge. If the current is led to the electrode at the edge and the electrode starts to dissolve at the edge to the insulating material it leads to a faster break up of the conductivity. The advantage of the present multilayer is that the conductivity stays stable because even if the electrode starts to dissolve at the edge to the insulating material the conductivity stays stable until the electrode dissolves completely towards the center. Vias can be used to connect traces on different metal layers or to connect an electrode to a metal trace.

FIG. 16 depicts a cross-sectional view of a multilayer structure. It shows as an example two layers of traces T and T2. Trace T has a direct contact with an electrode. Trace T2 also has a direct contact to the electrode E.

FIG. 17 depicts a cross-sectional view of a multilayer structure with inter layer vias. Vias allow connections between multiple conductor layer, here metal traces. FIG. 17 shows that via passes current through the center of the electrode and not from the edge of the electrode. This has a certain advantage because the edge of the electrode has the tendency to dissolve faster.

FIG. 18 shows a top view of a cochlear prosthesis molded into a helical shape. The cochlear electrode array which preferably contains polyimide can be molded in a silicone mold in a helix structure. The helix structure is advantageous to be implanted into the cochlear.

The implanted portion of the preferred cochlear prosthesis is preferably coated with a lubricious and/or hydrophilic coating, comprising hydrophilic polymer containing poly (N-vinyl lactams, poly(vinylpyrrolidone), polyethylene oxide), polypropylene oxide), polyacrylamides, cellulosics, methyl cellulose, polyanhydrides, polyacrylic acids, polyvinyl alcohols, polyvinyl ethers or mixtures thereof.

The above descriptions have been intended to illustrate the preferred and alternative embodiments of the invention. It will be appreciated that modifications and adaptations to such embodiments may be practiced without departing from the scope of the invention, such scope being most properly defined by reference to this specification as a whole and to the following claims.

The invention claimed is:

1. A cochlear electrode array adapted for cochlear stimulation comprising:
    a polymer base layer;
    high density patterned first metal traces deposited on said polymer base layer;
    a polymer interlayer deposited on said polymer base layer and said first metal traces;
    high density patterned second metal traces deposited on said polymer interlayer;
    a polymer top layer deposited on said polymer interlayer and said first and second metal traces; said polymer interlayer and said polymer top layer defining voids for electrodes;
    electrodes deposited on said first and second metal traces in said voids; and
    a skirt comprising a soft polymer, which is more compliant than said polymer base layer, surrounding the array and extending beyond its edges;
    wherein said array has a soft tip containing said soft polymer; and
    wherein said array is curved into a helical shape to approximate the shape of the cochlea.

2. The cochlear electrode array of claim 1 wherein said electrode have a surface coating.

3. The cochlear electrode array of claim 1 wherein said traces comprise platinum as a conductive layer.

4. The cochlear electrode array of claim 3 wherein said conductive layer further comprises adhesion layers on top and bottom sides of the conductive layer.

5. The cochlear electrode array of claim 3 wherein said adhesion layers comprise titanium.

6. The cochlear electrode array of claim 3 wherein said polymer base layer and said polymer top layer define voids to improve adhesion with said skirt.

7. The cochlear electrode array of claim 1 further comprising vias to connect said metal traces on different layers.

8. The cochlear electrode array of claim 1 further comprising a coating comprising a hydrophilic polymer selected from the group containing poly(N-vinyl lactams, poly(vinylpyrrolidone), poly(ethylene oxide), poly(propylene oxide), polyacrylamides, cellulosics, methyl cellulose, polyanhydrides, polyacrylic acids, polyvinyl alcohols, polyvinyl ethers or mixtures thereof.

9. The cochlear electrode array of claim 1 further comprising a cochleostomy grommet which includes an upper half and a lower half joined by a hinge.

10. The cochlear electrode array of claim 9, wherein said cochleostomy grommet is made from a single piece of biocompatible polymer.

* * * * *